(12) United States Patent
Backes

(10) Patent No.: US 10,124,842 B2
(45) Date of Patent: Nov. 13, 2018

(54) DEVICE AND METHOD FOR DETERMINING THE GROUND PRESSURE DISTRIBUTION IN A MOBILE WORK MACHINE

(71) Applicant: Manitowoc Crane Group France SAS, Dardilly (FR)

(72) Inventor: Bernd Backes, Oberthal (DE)

(73) Assignee: Manitowoc Crane Group France SAS, Dardilly (FR)

( * ) Notice: Subject to any disclaimer, the term of this patent is extended or adjusted under 35 U.S.C. 154(b) by 178 days.

(21) Appl. No.: 15/067,639

(22) Filed: Mar. 11, 2016

(65) Prior Publication Data

US 2016/0264196 A1 Sep. 15, 2016

(30) Foreign Application Priority Data

Mar. 11, 2015 (DE) .................. 10 2015 103 556

(51) Int. Cl.
*B62D 55/08* (2006.01)
*B62D 55/06* (2006.01)
(Continued)

(52) U.S. Cl.
CPC ............. *B62D 55/08* (2013.01); *B62D 55/06* (2013.01); *B62D 55/14* (2013.01); *G01N 3/08* (2013.01)

(58) Field of Classification Search
None
See application file for complete search history.

(56) References Cited

U.S. PATENT DOCUMENTS 3,994,352 A * 11/1976 Siorek ................ B60T 7/12
180/271
4,545,624 A * 10/1985 Van Ooyen ........... B62D 55/30
192/13 R
(Continued)

FOREIGN PATENT DOCUMENTS

DE 3711239 C2 10/1987
DE 69211843 T2 1/1997
(Continued)

OTHER PUBLICATIONS

European Search Report for related European Application No. 16159175.5, dated Oct. 3, 2016 (8 pages).
(Continued)

*Primary Examiner* — Harshad R Patel
*Assistant Examiner* — Tran M Tran
(74) *Attorney, Agent, or Firm* — Ramey & Schwaller, LLP; Craig Buschmann

(57) ABSTRACT

A tracked drive assembly for a work machine comprises a crawler frame, a crawler track, a drive wheel and a guide wheel, and an arrangement of running wheels coupled to the crawler frame, wherein the tracked drive assembly has a sensor system comprising a sensor for each of the outer running wheels of the running wheel arrangement, which are positioned or located adjacent to the drive wheel and the guide wheel, and at least one other running wheel which is arranged between the outer running wheels, wherein the force introduced into the crawler track via the respective running wheel can be determined by way of the sensor. A method for determining the ground pressure distribution below a work machine includes exposing the sensor to a compressive load at a running wheel.

9 Claims, 4 Drawing Sheets

(51) Int. Cl.
  *B62D 55/14* (2006.01)
  *G01N 3/08* (2006.01)

(56) References Cited

U.S. PATENT DOCUMENTS

| | | | | |
|---|---|---|---|---|
| 4,721,327 A * | 1/1988 | Chauveau | .......... | B62D 55/1125 |
| | | | | 280/124.129 |
| 5,390,996 A * | 2/1995 | Bliss | .................... | B62D 55/305 |
| | | | | 305/145 |
| 6,158,535 A * | 12/2000 | Porubcansky | ....... | B62D 55/084 |
| | | | | 180/9.1 |
| 6,431,665 B1 * | 8/2002 | Banerjee | ................ | B62D 55/30 |
| | | | | 180/9.1 |
| 6,857,489 B2 * | 2/2005 | Lakes | .................... | B62D 55/00 |
| | | | | 180/305 |
| 6,948,783 B2 * | 9/2005 | Hoff | ........................ | B62D 55/30 |
| | | | | 305/144 |
| 7,172,257 B2 * | 2/2007 | Tamaru | .................. | B62D 55/30 |
| | | | | 305/125 |
| 7,509,846 B2 * | 3/2009 | Matsumoto | ............. | G01L 5/167 |
| | | | | 73/116.07 |
| 7,828,162 B2 * | 11/2010 | Wiesbauer | ............ | B66C 23/185 |
| | | | | 212/238 |
| 8,579,057 B2 * | 11/2013 | Wagger | .................... | B60G 5/01 |
| | | | | 180/9.46 |
| 8,727,047 B2 * | 5/2014 | Janzen | ................. | B62D 55/116 |
| | | | | 180/9.1 |
| 8,985,250 B1 * | 3/2015 | Lussier | ................ | B62D 11/003 |
| | | | | 180/9.1 |
| 9,038,557 B2 * | 5/2015 | Smith | ..................... | B63B 59/10 |
| | | | | 114/222 |
| 9,284,166 B2 * | 3/2016 | Stuehrwoldt | ............ | B66C 23/40 |
| 9,334,001 B2 * | 5/2016 | Lussier | ................ | B62D 55/244 |
| 9,751,372 B2 * | 9/2017 | Traut | ................... | B60G 17/016 |
| 2002/0007973 A1 * | 1/2002 | Lakes | ................... | B62D 55/00 |
| | | | | 180/9.21 |
| 2011/0174555 A1 | 7/2011 | Willim | | |
| 2014/0090907 A1 * | 4/2014 | Stuehrwoldt | ........... | B66C 23/40 |
| | | | | 180/53.4 |
| 2017/0225727 A1 * | 8/2017 | Sauvageau | ............. | B62D 55/14 |

FOREIGN PATENT DOCUMENTS

| | | |
|---|---|---|
| DE | 202006017724 U1 | 4/2008 |
| DE | 202010001192 U1 | 6/2011 |
| EP | 1995159 A1 | 11/2008 |
| EP | 2977300 A1 | 1/2016 |
| JP | 55-11929 A | 1/1980 |

OTHER PUBLICATIONS

First Office Action with English translation for corresponding German Patent Application No. 102015103556.1, dated Nov. 23, 2015 (14 pages).

Notification of Reasons for Rejection for related Japanese Application No. 2016-045432, dated Dec. 6, 2016 (5 pages).

\* cited by examiner

DEVICE AND METHOD FOR DETERMINING THE GROUND PRESSURE DISTRIBUTION IN A MOBILE WORK MACHINE

RELATED APPLICATIONS

The present patent document claims the benefit of priority to German Patent Application No. 10 2015 103 556.1, filed Mar. 11, 2015, and entitled "Device and Method for Determining the Ground Pressure Distribution in a Mobile Work Machine," the entire contents of which is incorporated herein by reference.

BACKGROUND

The present invention relates to a tracked drive assembly for a mobile work machine, such as for example a crawler crane or crawler excavator, wherein said tracked drive assembly has a sensor system for determining the forces introduced into the ground via the tracked drive assembly. The invention also relates to a method for determining the ground pressure distribution and to a work machine controller which performs this method. The invention also relates to a work machine comprising a corresponding tracked drive assembly and a corresponding work machine controller.

In order to be able to use work machines such as for example crawler cranes or crawler excavators securely, it is necessary to determine the ground pressure permissible for operating the machine, i.e. the pressure which the ground beneath the machine will still withstand. The permissible ground pressure often has to be estimated, wherein even values for the permissible ground pressure specified in corresponding tables can only serve as rough guide values. Information on the pressure which the machine actually exerts on the ground beneath it is also required in order to prevent the permissible ground pressure from being exceeded.

In the case of mobile cranes, this has for example been managed by measuring the load accommodated by the crane, which allows an estimation of the ground pressure generated, wherein the data thus obtained are fed to a work machine controller which blocks crane functions which would cause the permissible ground pressure to be exceeded. Despite these security measures, instances of damage have in the past occurred which were due to the permissible ground pressure being exceeded.

DE 20 2010 001 192 U1 discloses a crawler drive assembly in which a means for adjusting the bearing area of the crawler frame is provided in each of the front region and rear region of the crawler frame, wherein at least one force measuring system, for measuring the forces applied in the region of the means, is provided.

DE 37 11 239 C2 discloses a device for securing mobile crawler transporters against tipping while loading and/or moving the load, wherein a base frame is connected to the drive assembly via hydraulic or pneumatic cylinder piston units, and pressure measuring devices are connected to the working spaces of the cylinder piston units.

BRIEF SUMMARY

It is an object of the present invention to increase the degree of security when using mobile work machines.

This object is solved by the subject-matter of independent patent claims 1 and 7.

In accordance with the present invention, at least one tracked drive assembly is provided for a work machine, in particular for a crawler crane or crawler excavator, wherein said tracked drive assembly comprises a crawler frame, a crawler track, a drive wheel and a guide wheel, and an arrangement of running wheels coupled to the crawler frame, wherein the tracked drive assembly also has a sensor system comprising a sensor for each of the outer running wheels, which are positioned or located adjacent to the drive wheel and the guide wheel, and at least one other running wheel which is arranged between the outer running wheels, wherein the force introduced into the crawler track via the respective running wheel can be determined by means of said sensor.

Thus, in a tracked drive assembly in accordance with the invention, if at least three running wheels are provided, it is then precisely the forces currently being introduced into the crawler track via the respective running wheels and consequently via the crawler track into the ground which are measured by means of a sensor system. If the geometry of the crawler track is known, i.e. the bearing area available for introducing the force into the ground, then the currently prevailing ground pressure distribution can be deduced.

It is also possible for the forces transmitted via each of the individual running wheels to be detected not only for three or more running wheels of a tracked drive assembly but rather for all the running wheels and/or for the entire arrangement of running wheels of the tracked drive assembly. The accuracy with which the ground pressure distribution is determined also increases as the number of running wheels monitored by sensors increases. The latter need not then be interpolated for example across the regions comprising running wheels for which a sensor is not provided.

In the present invention, multiple running wheels can be monitored jointly by means of at least one sensor. Multiple running wheels could thus for example be combined to form groups, wherein the force introduced into the crawler track via the respective groups is determined by means of at least one sensor.

It is likewise possible within the framework of the present invention to provide at least one proprietary sensor for each running wheel, wherein the force introduced into the crawler track via the respective running wheel is detected by means of said sensor. Since individual sensors provide mutually independent measurement values, this enables the ground pressure distribution across the running wheel arrangement of the tracked drive assembly to be determined to a high degree of accuracy.

It should also be noted that the present invention not only enables the ground pressure distribution which actually exists to be determined directly but also enables the ground pressure distribution which currently exists to be determined in real time.

Any sensors which are suitable for measuring the pressure forces introduced into the ground via the respective running wheel and the crawler track may be considered for this purpose, such as for example sensors which detect bending stresses, torsional stresses, tensile stresses or compressive stresses on the components provided with the sensors, i.e. the sensor system of the tracked drive assembly in accordance with the invention can have at least one sensor in a component of the tracked drive assembly which is exposed to the load of at least one running wheel. Accordingly, parts of the crawler track can be fitted with sensors. Additionally or alternatively, it is also possible to provide sensors for components of the tracked drive assembly which are situated at any point in the path of force between the points at which the tracked drive assembly is bolted to the crawler middle piece, and the running wheels. As already mentioned, it is possible in accordance with the present invention to use any type of sensor which is suitable for deducing the pressure forces introduced into the ground. One or more pressure sensors can thus for example be provided for suitable components which are exposed to compressive loads. Similarly, components which are exposed to tensile, bending or torsional stresses can however also be fitted with sensors which measure the corresponding tensile, bending or torsional stresses.

By measuring the load exposure of the component which is generated by the crane and the accommodated load and transmitted via the at least one running wheel, it is possible to directly deduce the pressure force which is introduced into the ground from the respective running wheel via the crawler track.

In accordance with the invention, a sensor—in particular, a pressure sensor—can then be provided which is integrated into the drive assembly box of the crawler frame above the respective running wheel axle. This sensor can in particular abut and/or adjoin the respective running wheel axle.

It is also possible to provide multiple sensors, in particular pressure sensors, for each running wheel. It is then for example possible to integrate a sensor, on each of the two sides of the running wheel axle, in the drive assembly box.

Another aspect of the present invention relates to a method for determining the ground pressure distribution below a work machine, in particular a crawler crane or crawler excavator, having at least one tracked drive assembly comprising a crawler frame, a crawler track, a drive wheel and a guide wheel, and an arrangement of running wheels coupled to the crawler frame, wherein the tracked drive assembly has a sensor system comprising a sensor for each of the outer running wheels, which are positioned or located adjacent to the drive wheel and the guide wheel, and at least one other running wheel which is arranged between the outer running wheels, comprising the steps of: determining the forces introduced into the crawler track, for the running wheels, by means of the respective sensors; and determining the ground pressure distribution for at least one tracked drive assembly of the work machine from the forces determined.

The method in accordance with the invention can incorporate a tracked drive assembly such as has been described above. The bearing area, i.e. the predetermined geometry of the tracked drive assembly, is required—in addition to measuring the forces—in order to determine the ground pressure. On the basis of the information on the current ground pressure (distribution) obtained by the method in accordance with the invention, it is possible to realise a load torque limit which can be used alongside other types of load torque limit in a crane in accordance with statutory regulations. The method in accordance with the invention can thus also comprise at least one additional step which provides for suppressing crane functions which would cause a maximum permissible ground pressure to be exceeded.

All the steps of the method in accordance with the invention can be performed by a computer which forms part of a work machine controller.

Another aspect of the present invention relates to a work machine, in particular a crawler crane or crawler excavator, comprising at least one tracked drive assembly as described above and/or a work machine controller as described above.

BRIEF DESCRIPTION OF THE DRAWINGS

Preferred embodiments of the present invention are explained in the following on the basis of the enclosed drawings. The invention can comprise the features disclosed here, individually and in any expedient combination. There is shown.

DETAILED DESCRIPTION

Figure 1:
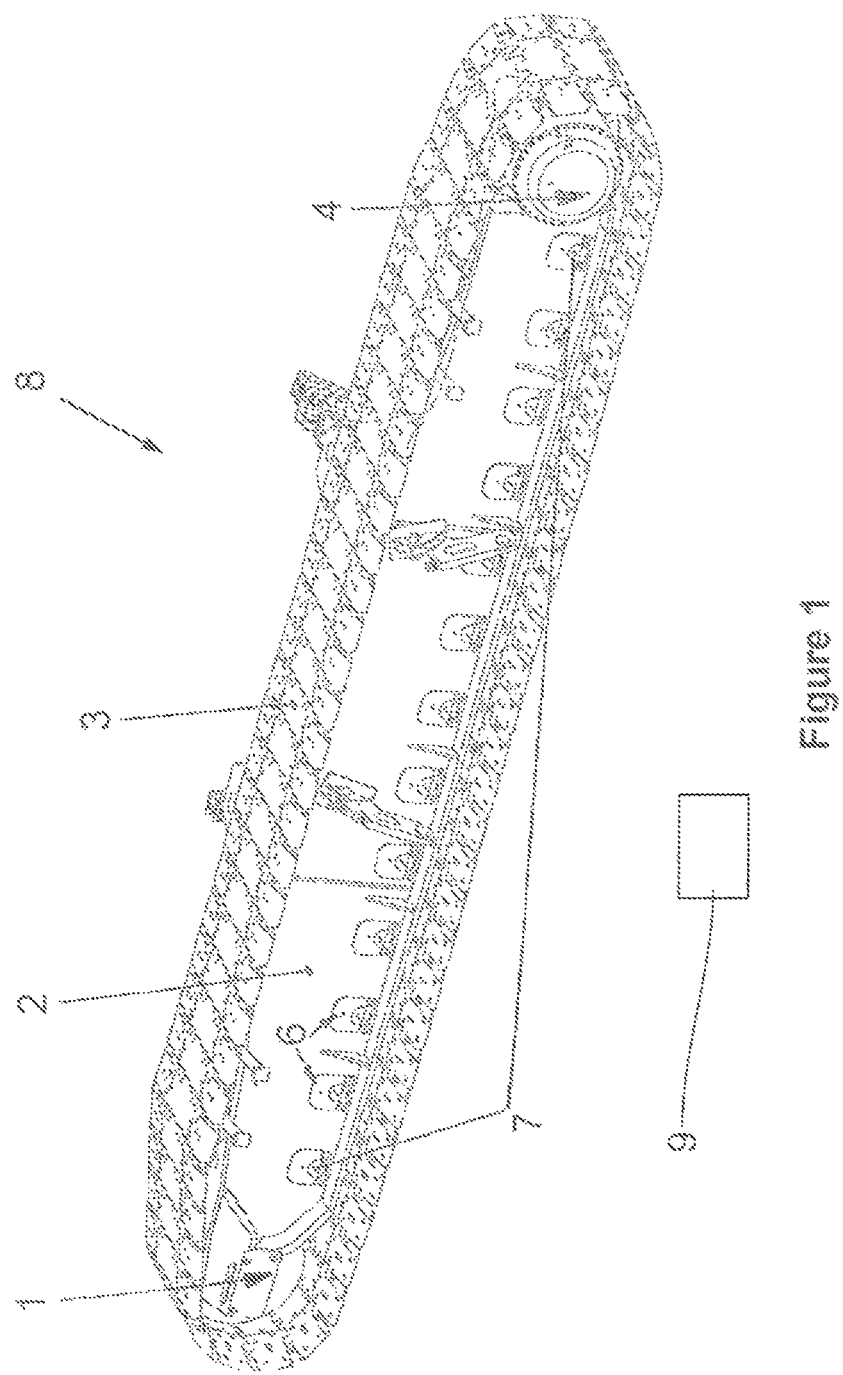
FIG. 1 is a perspective view of an embodiment of the tracked drive assembly in accordance with the present invention.

As can be seen in FIGS. 1 to 4, the embodiment of the tracked drive assembly 8 in accordance with the invention which is shown has multiple or an arrangement of running wheels 5 (which cannot be seen in FIG. 1, but is illustrated in outline in FIG. 2) which each rotate about a running wheel axle 7 of their own. The drive wheel 4 is situated at the rear end of the tracked drive assembly 8, shown on the right in FIG. 1, while the guide wheel 1 is situated at the front end of the tracked drive assembly 8, shown on the left in FIG. 1. The multi-link crawler track 3 extends around the crawler frame 2 and is driven by the drive wheel 4. Both the force of the weight of the work machine and the force of the weight of the load accommodated by the work machine is introduced into the ground below the crawler track 3 via the crawler frame 2, the running wheel axles 7, the running wheels 5 and the crawler track 3.

Figure 2:
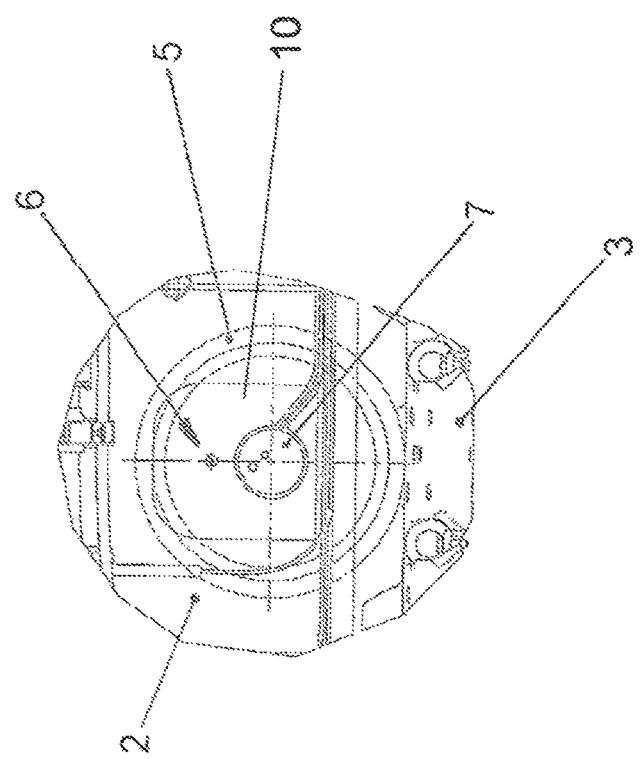
FIG. 2 is an enlarged view of the tracked drive assembly according to FIG. 1, in the region of a running wheel axle.
Figure 3:
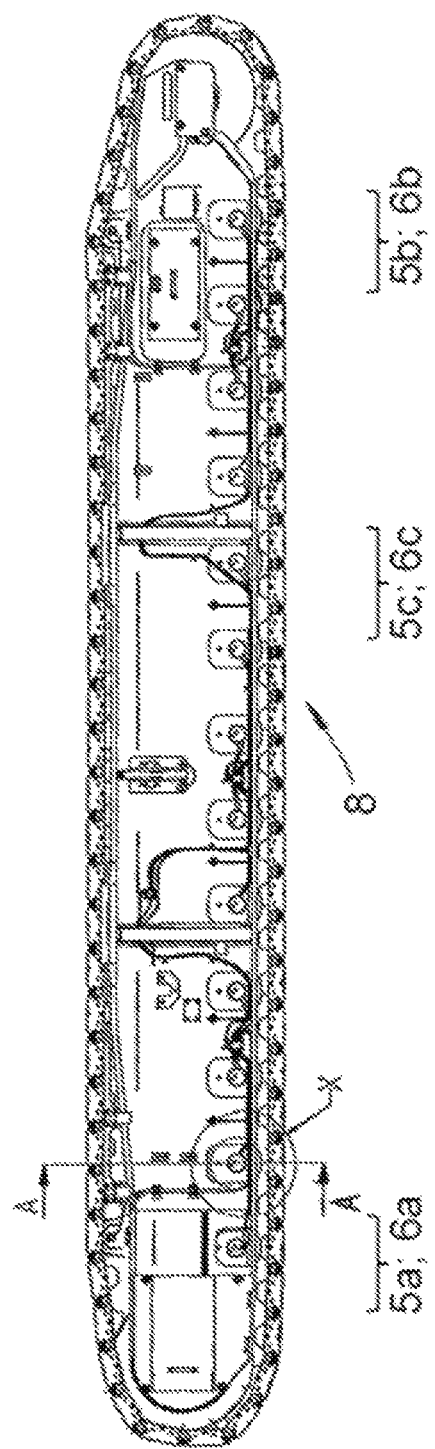
FIG. 3 is a lateral view of the tracked drive assembly according to FIG. 1.

As can be seen in FIGS. 1 and 2, a pressure sensor 6 is situated centrally above each of the running wheel axles 7, in a corresponding bore in the crawler frame 2. The pressure sensor 6 can then be integrated into the drive assembly box 10 of the crawler frame 2 above the respective running wheel axle 7, as illustrated in FIGS. 2 and 4.

Figure 4:
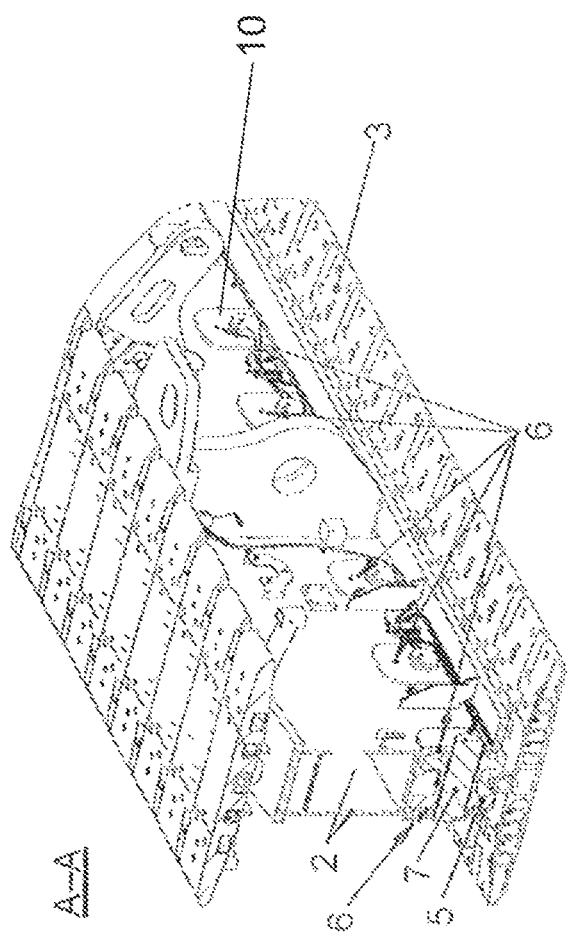
FIG. 4 is a cross-section A-A through the tracked drive assembly according to FIG. 3.

It is also evident from FIG. 4 that a pressure sensor 6 is provided above both ends of each of the running wheel axles 7, in the crawler frame 2, in the embodiment show. It can be seen in FIG. 4 that sensors 6 are provided above the respective running wheel axles 7 for all of the running wheels 5 of the tracked drive assembly 8. An outer running wheel which is positioned or located adjacent to the guide wheel 1 (FIG. 1), and a sensor which is assigned to this running wheel, are indicated by the reference signs 5a and 6a, respectively, while another outer running wheel which is positioned or located adjacent to the drive wheel 4, and the sensor which is assigned to this another outer running wheel, are indicated by 5b and 6b, respectively. Any running wheel which is arranged between the outer running wheels 5a and 5b, and the sensor which is assigned to this running wheel, are indicated by 5c and 6c, respectively. While the reference signs 5 and 6 denote any running wheels and sensors, respectively, the reference signs 5a and 6a always refer to the outermost running wheel which is positioned or located adjacent to the guide wheel 1, and the corresponding sensor, respectively, while the reference signs 5b and 6b denote the running wheel which is positioned or located adjacent to the drive wheel 4, and the corresponding sensor, respectively. The reference signs 5c and 6c have been allocated for any running wheel arranged between the two outer running wheels 5a and 5b, and a corresponding sensor.

It will be evident that the forces introduced into the crawler track 3 via the individual running wheels 5 expose the crawler frame 2 to a pressure load above the respective running wheel axles 7. The pressure sensors 6 arranged above the respective running wheel axles 7 therefore provide mutually independent measurement values for each running wheel 5, which enable the forces introduced into the crawler track 3 by means of the respective running wheels 5 to be directly deduced with a work machine controller 9 (FIG. 1). Since each running wheel 5 has its own sensor 6 in the example embodiment shown, it is possible to calculate not only the overall pressure exerted on the ground below via the tracked drive assembly 8 but in particular also the distribution of the ground pressure over the tracked drive assembly 8 when the individual running wheels 5 are exposed to loads of different magnitude.

The invention claimed is:

1. A tracked drive assembly for a crawler crane comprising a crawler frame, a crawler track, a drive wheel and a guide wheel, and an arrangement of running wheels coupled to the crawler frame, wherein the arrangement of running wheels comprises (a) an outer running wheel positioned adjacent to the drive wheel; (b) another outer running wheel positioned adjacent to the guide wheel; and (c) at least one running wheel which is arranged between the outer running wheel and the another outer running wheel, wherein the tracked drive assembly has a sensor system comprising at least one sensor for each of the outer running wheel, the another outer running wheel, and the at least one running wheel, wherein a force can be determined by the at least one sensor, said force being introduced into the crawler track via the respective outer running wheel, via the another outer running wheel, and via the at least one other running wheel, wherein the at least one sensor comprises a pressure sensor in a component of the tracked drive assembly which is exposed to a compressive load of the at least one running wheel, wherein said component of the tracked drive assembly is a drive assembly box of the crawler frame above an axle of the at least one running wheel, wherein the pressure sensor is integrated into said drive assembly box, wherein the pressure sensor includes a pair of pressure sensors, wherein one pressure sensor of the pair of pressure sensors is positioned in the drive assembly box on one side of the axle of the at least one running wheel and the other pressure sensor of the pair of pressure sensors is positioned on the other side of the axle of the least one running wheel.

2. The tracked drive assembly according to claim 1, wherein the at least one running wheel comprises a plurality of running wheels arranged between the outer running wheel and the another outer running wheel and wherein the sensor system comprises the at least one sensor for each running wheel of the plurality of running wheels.

3. The tracked drive assembly according to claim 1, further comprising a crawler crane to which the tracked drive assembly is coupled.

4. A method for determining a ground pressure distribution below a crawler crane, having at least one tracked drive assembly comprising a crawler frame, a crawler track, a drive wheel and a guide wheel, and an arrangement of running wheels coupled to the crawler frame, wherein the arrangement of running wheels comprises (a) an outer running wheel positioned adjacent to the drive wheel; (b) another outer running wheel positioned adjacent to the guide wheel; and (c) at least one running wheel which is arranged between the outer running wheel and the another outer running wheel, wherein the tracked drive assembly has a sensor system comprising at least one sensor for each of the outer running wheel, the another outer running wheel, and the at least one running wheel, wherein the at least one sensor comprises a pressure sensor in a component of the tracked drive assembly which is exposed to a compressive load of the at least one running wheel, wherein said component of the tracked drive assembly is a drive assembly box of the crawler frame above an axle of the at least one running wheel, wherein the pressure sensor is integrated into said drive assembly box, wherein the pressure sensor includes a pair of pressure sensors, wherein one pressure sensor of the pair of pressure sensors is positioned in the drive assembly box on one side of the axle of the at least one running wheel and the other pressure sensor of the pair of pressure sensors is positioned on the other side of the axle of the least one running wheel comprising the steps of:
determining a force introduced into the crawler track via the arrangement of running wheels with the respective sensors; and
determining the ground pressure distribution for the at least one tracked drive assembly of the work machine from the forces determined.

5. The method according to claim 4, further comprising performing the steps of the method with a work machine controller.

6. A tracked drive assembly for a crawler crane comprising a crawler frame, a crawler track, a drive wheel and a guide wheel, and an arrangement of running wheels coupled to the crawler frame, wherein at least a plurality of the running wheels in the arrangement of running wheels form at least one group of running wheels, wherein the tracked drive assembly has a sensor system comprising at least one sensor for the at least one group of running wheels, wherein a force can be determined by the at least one sensor, said forced being introduced into the crawler track via the at least one group of running wheels, wherein at least one sensor comprises a pressure sensor in a component of the tracked drive assembly which is exposed to a compressive load of the at least one group of running wheels, wherein said component of the tracked drive assembly is a drive assembly box of the crawler frame above an axle of the at least one group of running wheels, wherein the pressure sensor is integrated into said drive assembly box, wherein the pressure sensor includes a pair of pressure sensors, wherein one pressure sensor of the pair of pressure sensors is positioned in the drive assembly box on one side of the axle of the at least one group of running wheels and the other pressure sensor of the pair of pressure sensors is positioned on the other side of the axle of the least one group of running wheels.

7. The tracked drive assembly according to claim 6, wherein the at least one group of running wheels comprises a plurality of groups of running wheels and wherein the at least one sensor comprises a plurality of sensors with one sensor of the plurality of sensors for each group of running wheels.

8. The tracked drive assembly according to claim 6, wherein the at least one sensor comprises a plurality of sensors with one sensor of the plurality of sensors for each running wheel within the at least one group of running wheels.

9. The tracked drive assembly according to claim 6, further comprising a crawler crane to which the tracked drive assembly is coupled.

* * * * *